United States Patent [19]

Stanker et al.

[11] Patent Number: 5,614,408
[45] Date of Patent: Mar. 25, 1997

[54] MONOCLONAL ANTIBODIES TO POTATO, TOMATO, AND EGGPLANT GLYCOALKALOIDS AND ASSAYS FOR THE SAME

[75] Inventors: Larry H. Stanker; Carol K. Holtzapple, both of College Station, Tex.; Mendel Friedman, Moraga, Calif.

[73] Assignee: The United States of America as represented by the Secretary of Agricultural, Washington, D.C.

[21] Appl. No.: 544,748

[22] Filed: Oct. 18, 1995

[51] Int. Cl.$^6$ .............................. C07K 16/16; C12N 5/12; G01N 33/53
[52] U.S. Cl. .................. 435/341; 436/518; 530/388.5; 530/389.1; 435/7.1
[58] Field of Search .............................. 435/7.1, 240.27; 530/388.5, 389.1; 436/518

[56] References Cited

PUBLICATIONS

Stanker, Larry H., Kamps–Holtzapple, Carol, Freidman, Mendel, "Development and Characterization of Monoclonal Antibodies That Differentiate between Potato and Tomato Gylcoalkaloids and Aglycons." Journal of Agricultural and Food Chemistry Oct. 19, 1994, vol. 42, pp. 2360–2366, American Chemical Society.

Thomson, Carrie A., Sporns, Peter, "Fluorescence Polarization Immunoassays for potato Glycoalkaloids," Journal of Agricultural and Food Chemistry, 1995, vol. 43, pp. 254–260, American Chemical Society.

Pihak, Leslie C., Sporns, Peter, "Enzyme Immunoassay for Potato Glycoalkaloids", Journal of Agricultural and Food Chemistry, 1992, vol. 40, pp. 2533–2540, American Chemical Society.

Phlak, Leslie, and Sporns, Peter, "Development and Production of Monoclonal Antibodies for the Measurement of Solanidine Potato Glycoalkaloids", American Potato Journal, 1994, vol. 71, No. 5, pp. 297–313.

Stanker, Larry H., Kampa–Holtzapple, C, Friedman, M., Abstract entitled "Monoclonal Antibodies to Potato Glycoalkaloids and Molecular Modeling Studies of Cross–reacting Compounds", Presented at the annual meeting of the American Chemical Society in Mar. 1993.

Friedman, Mendel, and Levin, Carol E., "α–Tomatine Content in Tomato and Tomato Products Determined by HPLC with Pulsed Amperometric Detection", Journal of Agricultural and Food Chemistry, 1995, vol. 43, No. 6, pp. 1507–1511.

*Primary Examiner*—Frank C. Eisenschenk
*Attorney, Agent, or Firm*—M. Howard Silverstein; Randall E. Deck; John D. Fado

[57] ABSTRACT

A hybridoma cell lines is described which produces and secretes a monoclonal antibody which selectively binds to the glycoalkaloids of potatoes, tomatoes, and eggplants, as well as their corresponding aglycones. Glycoalkaloids of potatoes, tomatoes, and/or eggplants in biological samples may be detected and quantified by contacting the sample with the antibodies to form a glycoalkaloid/antibody immunocomplex when the glycoalkaloids are present, which immunocomplex may then be detected. The monoclonal antibody may also be incorporated into kits for the detection and quantification of glycoalkaloids in plants, foods, and body tissues and fluids.

6 Claims, No Drawings

MONOCLONAL ANTIBODIES TO POTATO, TOMATO, AND EGGPLANT GLYCOALKALOIDS AND ASSAYS FOR THE SAME

BACKGROUND OF THE INVENTION

1. Field of the Invention

This invention relates to a hybridoma cell line and monoclonal antibody produced therefrom which may be used to detect potato, tomato, and/or eggplant glycoalkaloids.

2. Description of the Prior Art

Alkaloids are potentially toxic nitrogen-containing secondary plant metabolites found in numerous plant species, including potatoes and tomatoes (Friedman, 1992, *J. Agric. Food Chem.*, 40:419–423, and *ACS Symp. Ser.*, No. 406, 429–462). The two major glycoalkaloids in commercial potatoes (*Solanum tuberosum*), α-chaconine and α-solanine, are both glycosylated derivatives (triosides) of the aglycon solanidine. Wild potatoes (*Solanum chacoense*) and eggplants (*Solanum melongena*) produce the glycoalkaloid solasonine. The major glycoalkaloid in tomatoes (*Lycopersicon esculentum*), α-tomatine, is the glycosylated derivative of the aglycon tomatidine.

The potato glycoalkaloids are thought to function as a defense against insects and other pests (Norris, 1986, In *Chemistry of Plant Protection*, Haug and Hoffman eds., Springer Verlag, Berlin, Germany, pp. 97–146). Because wild potatoes often contain higher glycoalkaloid levels than commercial varieties, they have been used by plant breeders attempting to generate improved cultivars. Such cultivars, however, can have glycoalkaloid levels above 20 mg/100 g of tuber, the generally accepted cutoff level between safe and unsafe potatoes (Slanina, 1990, Food Chem., 28:759–761; and Van Gelder, 1991, In *Handbook of Natural Toxins*, Vol. 6, *Toxicology of Plant and Fungal Compounds*, Keeler and Tu, eds., Marcel Dekker Inc., New York, pp. 101–134). This guideline limiting the glycoalkaloid content of new potato cultivars has been recommended because of the potential human toxicity of these compounds, including reported deaths (McMillan and Thompson, 1979, Quaterly Journal of Medicine, 48:227–243; and Morris and Lee, 1984, Food Technology in Australia, 36:118–124).

Detection of glycoalkaloids in potato and tomato plants is of interest because of the toxic nature of these compounds. Traditional methods to detect these plant constituents are often complicated and time consuming, and they rely upon the use of large amounts of organic solvents. In addition, the reported methods are not readily field portable, and most require sophisticated and expensive equipment and trained personnel to run the assays and interpret the results.

Methodologies that have been disclosed for the analysis of glycoalkaloids and related compounds include gas chromatography (Herb et al., 1975, J. Agric. Food Chem., 23:520–523; Lawson et al., 1992, J. Agric. Food Chem., 40:2186–2191; and Van Gelder et al., 1989, J. Chromatogr., 482:13–22), and high-performance liquid chromatography (Bushway, 1982, J. Liq. Chromatogr., 5:1313–1322; Bushway et al., 1979, J. Chromatogr., 178:533–541; and 1986, J. Agric. Food Chem., 34:277–279; Carman et al., 1986, J. Agric. Food Chem., 34:279–282; Friedman and Levin, 1992, J. Agric. Food Chem., 40:2157–2163; Morris and Lee, 1981, J. Chromatogr., 219:403–410; and Osman and Sinder, 1989, J. Chromatogr., 479:189–193).

Immunoassays for potato glycoalkaloids have been described. Ward et al. (1988, Food Addit. Contam., 5:621–627) and Plhak and Sporns, 1992, J. Agric. Food Chem., 40:2533–2544) described polyclonal antisera raised using immunogens produced by complex conjugation strategies. These immunogens were produced by first cleaving the carbohydrate side chain by periodate to aldehyde groups, followed by Schiff's base formation with BSA and reduction of the Schiff's bases by sodium borohydride. Other immunoassays for potato glycoalkaloids have also been described by Morgan et al. (1983, J. Sci. Food Agric., 34:593–598; and 1985, In *Immunoassays in Food Analysis*, Morris and Clifford eds., Elsevier Applied Science Publishers, London, UK, pp. 187–195), Plhak and Sporns (1994, Am. Potato J., 71:297–313), Thomson and Sporns (1995, J. Agric. Food Chem., 43:254–260) and Vallejo and Ercegovich (1978, In *Methods and Standards for Environmental Measurements*, Publication 519, National Bureau of Standards, Washington, D.C., pp. 333–340). Barbour et al. (1991, Rev. Pesticide Toxicol., 1:289–303) also described an immunoassay for the tomato glycoalkaloid, α-tomatine. However, the above studies all used the glycoalkaloid itself, or a modified glycoalkaloid as immunogen, linking to the carrier protein via a modification in the sugar. Generally, these immunogens have not resulted in antibodies of sufficiently high affinity to be suitable for use in commercial assays.

SUMMARY OF THE INVENTION

We have now discovered a hybridoma cell line which produces and secretes a monoclonal antibody which selectively binds to the glycoalkaloids of all of potatoes, tomatoes, and eggplants, as well as their corresponding aglycones. Glycoalkaloids of potatoes, tomatoes, and/or eggplants in biological samples may be detected and quantified by contacting the sample with the antibody to form a glycoalkaloid/antibody immunocomplex when the glycoalkaloids are present, which immunocomplex may then be detected. The monoclonal antibody may also be incorporated into kits for the detection and quantification of glycoalkaloids.

It is an object of this invention to provide a hybridoma cell line that produces and secretes a high affinity monoclonal antibody which selectively binds the glycoalkaloids of potatoes, tomatoes, and eggplants.

Another object of this invention is to provide immunoassay methods for the measurement of potato, tomato, and/or eggplant glycoalkaloids in biological samples.

A further object is to provide kits useful for the assay of potato and/or tomato glycoalkaloids which include the monoclonal antibody described herein.

Other objects and advantages of this invention will become readily apparent from the ensuing description.

DETAILED DESCRIPTION OF THE INVENTION

In accordance with this invention, we have created a hybridoma cell line that produces a monoclonal antibody which selectively binds the glycoalkaloids of potatoes, tomatoes, and eggplants, as well as their corresponding aglycones. This antibody, which has been designated Sol-129, possesses improved specificity and increased affinity for the glycoalkaloids than previously described antibodies. Even more surprising, this monoclonal antibody selectively binds to the glycoalkaloids of both potatoes and tomatoes. The novel antibody of this invention may be used to rapidly and accurately detect and quantify glycoalkaloids of any or all of potatoes, tomatoes, and eggplants, providing an indicator of the level of these potentially toxic metabolites in biological samples and in diests of animals and humans.

The above-mentioned hybridoma cell line which produces and secretes monoclonal antibody Sol-129 has been deposited under the Budapest Treaty in the American Type Culture Collection (12301 Parklawn Drive, Rockville, Md., 20852, USA) on Oct. 9, 1996, and has been assigned Deposit No. ATCC HB 12201.

In contrast to previously described hybridoma cell lines which were prepared using immunogens constructed from the glycoalkaloids per se, the hybridoma cell line of this invention was prepared from the aglycone of one of these compounds. Specifically, the immunization agent used herein was prepared by covalently conjugating an immunogenic carrier to solanidine, the common aglycone of the potato glycoalkaloids α-solanine and α-chaconine.

Hybridoma production, including the steps of immunizing an animal with the immunogen, recovering spleen lymphocytes therefrom, and fusing the splenocytes with continuously replicating myeloma cells to produce hybrid cells, was conducted using conventional techniques such as described by Kohler and Milstein [Nature, 256:495–497 (1975)], or Stanker et al. [U.S. patent application Ser. No. 08/081,591, filed Jun. 23, 1993], the contents of each of which are incorporated by reference herein. Hybridoma supernatants were screened for production of antibodies by direct-binding ELISA and competitive inhibition ELISA.

One monoclonal antibody, designated Sol-129, exhibited a high affinity for the potato glycoalkaoids α-solanine and α-chaconine, their aglycone, solanidine, as well as solasonine, the glycoalkaloid of the wild potato and eggplant. Surprisingly, when examined for specificity to other glycoalkaloids, monoclonal antibody Sol-129 also specifically bound the tomato glycoalkaloid α-tomatine, and its corresponding aglycone, tomatidine. Moreover, this antibody bound the tomato glycoalkaloid with approximately the same affinity as the potato glycoalkaloids. As shown in Table 1 and described in detail in Example 2, when the sensitivity was measured at a high standard of accuracy ($IC_{50}$) by competitive inhibition ELISA, the detection limits of the antibody for α-solanine, α-chaconine, and α-tomatine, were 2.6, 2.8 and 5.4 ppb, respectively (using 100 μl samples added to microtiter plate wells). Without being limited thereto, glycoalkaloids and their aglycones which may be detected include solasonine and solasodine, and particularly α-tomatine and tomatidine, and α-solanine, α-chaconine and solanidine.

The structures of these aglycones and glycoalkaloids are shown below. Solanidine, α-solanine, and α-chaconine are of the formula:

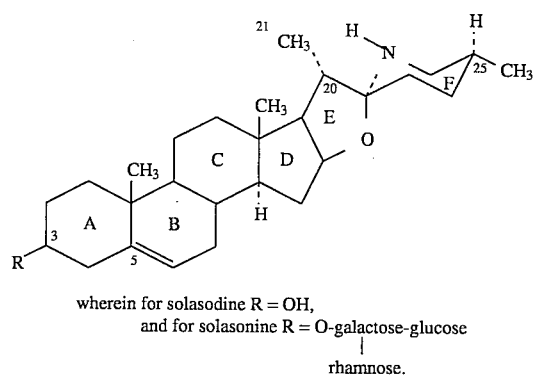

wherein for solanidine R = OH,
for α-solanine R = O-galactose-glucose
|
rhamnose,
and for α-chaconine R = O-galactose-rhamnose
|
rhamnose.

Solasodine and solasonine are of the formula:

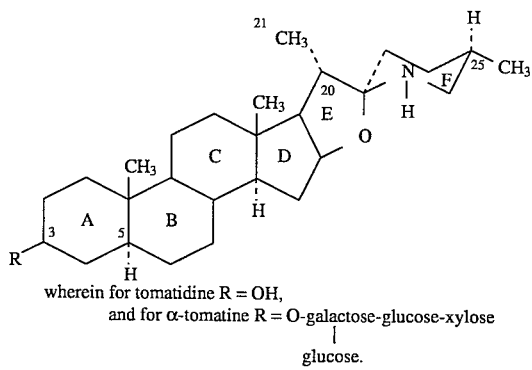

wherein for solasodine R = OH,
and for solasonine R = O-galactose-glucose
|
rhamnose.

Finally, tomatidine and α-tomatine the structures are of the formula:

wherein for tomatidine R = OH,
and for α-tomatine R = O-galactose-glucose-xylose
|
glucose.

Large quantities of monoclonal antibody Sol-129 may be produced by propogation of the hybridoma in tissue culture using well-known techniques. Alternatively, antibody may be produced within host animals, such as by ascites formation in syngenic mice. Monoclonal antibodies so produced may be purified, for example, by affinity chromatography on a protein A or G resin, or using glycoalkaloid bound to a resin.

Monoclonal antibody Sol-129 may be used to detect and/or quantify glycoalkaloids in unknown samples using a variety of conventional immunosorbent assays including but not limited to RIA or ELISA. A competitive inhibition ELISA similar to that used to screen the hybridomas as described in Example 2 is preferred. In this assay, a sample to be analyzed for a target glycoalkaloid or aglycone is incubated with the monoclonal antibody and a solid substrate coated with the same glycoalkaloid or aglycone. After incubation, the solid phase is drained and washed, and bound antibody on the substrate is detected. Detection of bound antibody may be accomplished by addition of enzyme-labeled anti-immunoglobulin antibodies followed by enzyme substrate. Horse radish peroxidase and its substrate, 2,2'-azinobis-3-ethylbenthiazolinesulfonic acid (ABTS) are preferred enzyme/substrate labels. However, it is understood that other enzyme/substrate labels or non-enzyme labels such as radiolabels or chromophores may also be used. Percent inhibition may be calculated as $(1-B/B_o) \times 100$, where B is the optical density (OD) of a well with a competitor and $B_o$ is the mean OD of the wells without competitor (control). The concentration of the glycoalkaloid in the sample may then be determined by reference to a standard curve. A standard curve relating the percent inhibition (amount of bound antibody) to glycoalkaloid concentration may be constructed from assays using known levels of glycoalkaloid.

In one alternative embodiment, glycoalkaloid may be determined by a competition ELISA such as described in Brandon et al. (U.S. Pat. No. 5,053,327, the contents of which are incorporated by reference herein) using the monoclonal antibody attached to a solid support. For example, the anti-glycoalkaloid antibody may be immobilized on a solid support such as a bead or microtiter well. The unknown sample to be analyzed (or analytical standards of glycoalkaloid) are then added with enzyme or radiolabeled glycoalkaloid, and the amount of labeled glycoalkaloid bound to the antibody is measured, using a substrate when the label is an enzyme. The amount of the glycoalkaloid in the sample is inversely proportional to the amount of bound labeled glycoalkaloid. In another alternative, the monoclonal antibody may be attached to a solid support for use in conventional double-antibody sandwich ELISA procedures.

With any of the above-described assay formats, the monoclonal antibody of the invention may be incorporated into kits, alone or preferably together with any other necessary reagents. A preferred kit for use herein comprises a first container including the monoclonal antibody, a second container including detection means effective for detecting bound antibody, and a solid phase support having the glycoalkaloid(s) of interest attached thereto.

Determination of potato, tomato and/or eggplant glycoalkaloids in a variety of biological samples may be conducted using the above-described assays with minimal sample preparation and using simple extraction procedures. In one embodiment, potato, tomato or eggplant samples may be homogenized in acetic acid, centrifuged, and the liquid phase recovered. After neutralizing the pH, this supernatant may then be assayed as described hereinabove. Alternatively, the glycoalkaloids may be extracted using alcohol as described by Plhak and Sporns (1992, ibid). Without being limited thereto, the assays are particularly advantageous for determining glycoalkaloid levels in potatoes, tomatoes or eggplants, cultivars of potatoes, tomatoes or eggplants produced in breeding programs, foods or processed potato, tomato or eggplant products (e.g., soups, sauces, juice, or ketchup), and animal or human tissues or fluids. Furthermore, because some foods and body tissues or fluids may contain glycoalkaloids from more than one of potatoes, tomatoes, and eggplants, the monoclonal antibody may be used to measure total glycoalkaloid contents. When analyzing these samples, monoclonal antibody Sol-129 may be used with other monoclonal antibodies specific only for potato or tomato glycoalkaloids, such as described in Example 2, to measure both specific and total glycoalkaloids.

Another application of the monoclonal antibody is affinity purification of glycoalkaloids. The antibody may be bound to a matrix, column, or other support by well-known techniques and used to recover or remove the glycoalkaloids from any desired material. Alternatively, the monoclonal antibody may be incorporated into sensors such as solid phase electronic devices for detection of glycoalkaloids in sample materials.

The following examples are intended only to further illustrate the invention and are not intended to limit the scope of the invention which is defined by the claims.

EXAMPLES

The preparation of the immunogen, generation and screening of the hybridomas, and assays for potato and tomato glycoalkaloids in the following Examples 1–3 are described in Stanker et al. (1994, J. Agric. Food Chem., 42:2360–2366), the contents of which is incorporated by reference herein.

Example 1

Immunogen Production

Fifty mg of solanidine (Sigma Chemical Co., St. Louis, Mo.) was mixed with 37.5 mg succinic anhydride in 750 µl anhydrous pyridine and refluxed overnight to form the hemisuccinate. The solanidine hemisuccinate was purified by thin-layer chromatography on silica gel 60 F254 plates using a 75:25 chloroform-methanol solvent system, and then conjugated to bovine serum albumin (BSA) and to keyhole limpet hemocyanin (KLH) as follows. The KLH and BSA were dissolved in 25% dimethyl formamide (DMF) (5 mg/ml for the KLH and 10 mg/ml for the BSA). One hundred µl of solanidine hemisuccinate (7 mg in DMF) was mixed with 50 µl of DMF, 20 µl of N-hydroxysuccinimide (NHS) (3 mg) in DMF-$H_2O$ (50:50 v/v), and 20 µl of 1-ethyl-3-[3(dimethylamino) propyl]carbodiimide hydrochloride (EDC) (3 mg) in DMF-$H_2O$ (50:50 v/v) and incubated at ambient temperature for 60 minutes. The mixture was then split and 1 ml of the above KLH or BSA solution added. These were then allowed to incubate with stirring at ambient temperature overnight. The samples were dialyzed against deionized water for 3 days, changing the water every 12 hours. Conjugation of the hapten to the protein was confirmed by electrophoresis as described by Kamps-Holtzapple (1993, J. Immunol. Methods, 164:245–253).

Example 2

Hybridoma Production

Five, 6 month old BALB/c mice were injected with 50 µl of the solanidine-KLH conjugate mixed 1:1 with Ribi adjuvant (Ribi Immunochem Research Inc., Hamilton, Mont.). The mice received half the dose intraperitoneally and half intramuscularly every other week for a total of three injections. One month later, and 4 days prior to fusion, a selected mouse was given an intraperitoneal injection of 50 µl of solanidine-KLH conjugate in sterile saline. The spleen was removed and the splenocytes fused with SP2/O myeloma cells as described by Stanker et al. (1986, J. Immunol., 136:4174–4180), the contents of which are incorporated by reference herein. The fused cells were plated over 30 96-well microculture plates previously coated with mouse peritoneal exudate cells (macrophage) and grown under conditions described by Elissalde et al. (1993, J. Agric. Food Chem., 41:2167–2171), the contents of which are also incorporated by reference herein.

Screening. Eleven days after fusion, the hybridomas were screened for antibodies that were positive against solanidine. The modified direct-binding ELISA technique described below was used for screening hybridoma supernatants. Solanidine linked to BSA (SOL-BSA) served as the binding antigen in both the direct-binding ELISA and the competition ELISA (c-ELISA) described below (BSA is an extraneous protein because the immunogen was solanidine-KLH) to prevent detection of anti-KLH antibodies.

db-ELISA. A modification of a direct-binding ELISA described by Stanker et al. (1993, J. Agric. Food Chem., 41:1332–1336), the contents of which are incorporated by reference herein, was used to screen the culture fluids from the growing hybridomas for antibodies to solanidine. Microtiter plates (Nunc Maxisorb, Roskilde, Denmark; or Costar high binding plates, Costar Corp., Wilmington, Mass.) were coated with SOL-BSA by addition of 100 μl/well of a 1 μg/ml solution of SOL-BSA in distilled water. The SOL-BSA was incubated in uncovered plates at 37° C. for 18 hr to evaporate the liquid and allow the SOL-BSA to coat the bottom of the microtiter wells. The "coated" plates were then stored in sealed plastic bags at 4° C. and used within 2 weeks. Nonreacted sites on the plates were blocked by adding 400 μl of a 3% solution of nonfat dry milk (NFDM) in assay buffer (0.1M Tris, 0.15M NaCl, 10 mg/ml nonfat dry milk, 0.001% Tween 20, 0.02% sodium azide) and incubating the plates at room temperature for 1 hr. The blocking solution was then discarded and 100 μl of the hybridoma supernatant(s) or anti-solanidine Mab (from ascites fluid) was added, and the plates incubated for 1 hr at 37° C. After incubation, the plates were washed with a solution of 0.05% TWEEN-20 in water, and peroxidase conjugated goat anti-mouse antiserum (Sigma Inc., St. Louis, Mo.), diluted 1:500 in assay buffer, was then added to each well. Following a second 1 hr incubation at 37° C., the plates were washed as described above. Finally, the substrate, 2,2'-azino-bis(ethylbenzthiazole-6-sulfonic acid) (ABTS), was added. Absorbance was measured at 405 nm and the resulting data analyzed by computer using an Excel (Microsoft, Redmond, Wash.) spreadsheet program.

Approximately 130 wells contained hybridomas that secreted antibodies which recognized the solanidine-BSA conjugate as indicated by a positive response in the db-ELISA. Cells from these wells were expanded and subcloned twice by limiting dilution to ensure their monoclonal origin, and then evaluated for their ability to recognize unconjugated solanidine in a competitive inhibition ELISA (c-ELISA).

c-ELISA. The competitive inhibition ELISA for solanidine and other glycoalkaloids was carried out as previously described for other compounds by Stanker et al. (1993, ibid). Briefly, to each well of an antigen (glycoalkaloid or aglycone) coated, non-fat-milk-blocked, microtiter plate prepared as described in the db-ELISA was added 100 μl of assay buffer. Competitors (free solanidine and other glycoalkaloids and aglycones, and four structurally related steroids cholesterol, digitonin, βsitosterol, and stigmasterol, shown in Table 1) dissolved in 100 μl of assay buffer were added to the microassay plate and serially diluted (a 2-fold series). Next, 100 μl of assay buffer containing a predetermined amount of anti-solanidine monoclonal antibody prepared above was added to each well. The amount of anti-alkaloid antibody added was the concentration (dilution from tissue culture supernatant) resulting in approximately 50% of maximum binding or signal in a direct-binding ELISA where no competitor was present. The plates were sealed with plastic wrap, incubated for 1 hr at 37° C., and then processed as described in the db-ELISA to detect bound antibody.

In each experiment, microtiter wells containing all components except competitor were prepared and the activity in these wells was taken to represent 100% activity (control wells). The test wells, each containing different amounts of competitor, were normalized to the 100% activity wells, and percent inhibition was calculated as:

$$[1-(A_{405} \text{ of test}/A_{405} \text{ of control})] \times 100$$

where $A_{405}$ is the absorbance at 405 nm. For greatest accuracy, the relative affinity of the antibodies was measured as the concentration of free glycoalkaloid added to the wells that resulted in at least 50% inhibition ($IC_{50}$) of control activity.

From this assay, eleven stable hybridomas producing antibodies that recognized unconjugated solanidine were subcloned. These eleven monoclonal antibodies, named with a Sol- prefix followed by the number of the well they were isolated from, are shown in Table 1.

Hybridoma Isotyping. The eleven monoclonal antibodies were isotyped according to manufacturer's recommendations, using the Fisher Biotech (Fisher Scientific, Pittsburgh, Pa.) isotyping kit. The antibodies were found to have either IgG1 or IgG2 heavy chains, and all had kappa light chains.

Results. The 50% inhibition of control ($ICs_{50}$) for the 11 antibodies isolated ranged from 2.5 to 1,000 ppb as shown in table 1. One antibody, Sol-129, had the lowest relative affinity for solanidine and clearly had the greatest relative sensitivity for the glycoalkaloids tested. Unexpectedly, a single antibody, again Sol-129, had an affinity for all of the potato or eggplant glycoalkaloids and aglycones tested, as well as the tomato glycoalkaloid α-tomatine and its aglycone tomatidine. Sol-129 was the only antibody capable of binding solasonine or α-tomatine or tomatidine. This was even more surprising considering that the potato aglycone solanidine was used as the immunogen. None of the eleven antibodies cross-reacted with the four structurally related steroids: cholesterol, digitonin, βsitosterol, or stigmasterol.

In review, as shown in Table 1, the monoclonal antibodies can be divided into four epitope groups on the basis of their reactivity with different glycoalkaloids. Group one includes antibodies which bind only the potato glycoalkaloids α-solanine and α-chaconine and their aglycone solanidine, but differentially bind to the aglycone (i.e. higher affinity) relative to the glycoalkaloids from the aglycone solanidine (including Sol-8, Sol-48, Sol-55, Sol-91 and Sol-106). The second group binds solanidine, α-solanine, and α-chaconine with similar relative affinities (Sol-59 and Sol-67). The antibodies of the third group bind only the aglycone solanidine (Sol-68 and Sol-71). The last group binds the potato glycoalkaloids α-solanine and α-chaconine and their corresponding aglycone solanidine, the eggplant glycoalkaloid solasonine and its aglycone solasodine, and the tomato glycoalkaloid α-tomatine and its aglycone tomatidine (Sol-129).

Example 3

Glycoalkaloid Assay

Five potato samples were analyzed for α-chaconine and α-solanine by c-ELISA using monoclonal antibodies Sol-106 and Sol-129 in comparison with an HPLC method. The following potato samples were used in these studies: 1) Klamath tuber flesh (no peel); 2) Russet whole tuber; 3) 3194 whole tuber; 4)Z whole tuber; and 5) Lenape peel (Friedman and Dao, 1992, J. Agric. Food Chem., 41:1397-1412).

Alkaloid Extraction. Freeze-dried samples (100 mg) of the potatoes were suspended in 5 ml of 2% acetic acid and extracted using a polytron homogenizer (3×30 sec. pulse). The resulting slurry was centrifuged at 1,000 g for 10 minutes. The supernatant was recovered and adjusted to pH 6.5–6.8 by addition of 1M $NH_4OH$. Between 2 and 10 μl of the extract was added to 100 μl of assay buffer and used in the c-ELISA described in Example 2.

HPLC Method. The α-chaconine and α-solanine contents of potato extracts were determined by HPLC as described by Friedman et al. (1993, J. Agric. Food Chem., 41:1397–1406).

The results of these experiments are shown in Table 2.

Example 4

Tomato samples were analyzed for α-tomatine, the major glycoalkaloid of tomatoes, using monoclonal antibody Sol-129. A number of samples representing different tomato cultivars and maturation stages, processed tomato products, and tomato plant root samples shown in Table 3 were analyzed by both c-ELISA and by HPLC.

Alkaloids Extraction. All samples were extracted using the method described by Friedman et al. (1994, J. Agric. Food Chem., 42:1959–1964), the contents of which are incorporated by reference herein. Fresh tomatoes were cubed and all samples were lyophilized. The dried tomatoes were then ground in an Omnimixer (Ivan Sorvall Inc., Newtown, Conn.) to pass through a 0.5 mm screen.

Tomatoes and other products were extensively extracted by a combination of liquid-liquid extraction and solid phase extraction to obtain an HPLC chromatogram that was free of interference. The steps required for solid phase extraction may be omitted when assaying only by ELISA. Samples were extracted by stirring 1 g in 20 ml of 1% acetic acid for 2 hr. An aqueous system was chosen to avoid formation of a gel by precipitation of pectic substances present in the extract. The suspension was then centrifuged for 10 min at 13 300 relative centrifugal force (RCF) and the supernatant filtered through a Whatman GF/C filter. The pellet was resuspended in 10 ml of 1% acetic acid, centrifuged, and filtered, and the two extracts were combined. This extract was further purified using solid phase extraction (SPE). A $C_{18}$ SPE tube, equipped with a 60 ml reservoir (Supelco), was conditioned with 5 ml of methanol followed by 5 ml of water. The aqueous extract (now about 30 ml) was applied and allowed to gravity drip. When the sample was fully absorbed onto the packing, the tube was washed with about 10 ml of water, followed by 5 ml of 30:70 acetonitrile-1% NH40H, and then 5 ml of water. The alkaloids were eluted with 10 ml of 70:30 acetonitrile-pH 3 citric acid/disodium phosphate buffer (as used in eluent). The organic solvent was then evaporated off. The aqueous residue was basified with ammonia water extracted twice into water-saturated butanol, using a separatory funnel. This sample was then dried on a rotovapor. The residue was taken up in 1 ml of 50% methanol-0.1% acetic acid and filtered through a 0.45 μm HV membrane obtained from Millipore (Bedford, Mass.). This filtrate was ready for HPLC injection.

These extracts were split and analyzed both by the c-ELISA and by HPLC.

c-ELISA. Samples were analyzed by c-ELISA using the procedure described in Example 2. The aliquot used in the c-ELISA was dried under a stream of nitrogen gas, resuspended in DMF (approximately 1 ml), diluted in assay buffer (usually a 1/1,000 dilution was made), and then further diluted an a 1:2 fashion in assay buffer. Unknown concentrations were determined by comparison to a percent $B/B_o$ standard curve near the $IC_{50}$ point ($B/B_o$ between 40–60%).

HPLC Method. The α-tomatine contents of the tomato extracts were determined by HPLC as described by Friedman et al. (1994, ibid).

The results of these experiments are shown in Table 3.

It is understood that the foregoing detailed description is given merely by way of illustration and that modifications and variations may be made therein without departing from the spirit and scope of the invention.

TABLE 1

Cross-Reactivity of the Different Monoclonal Antibodies: $IC_{50}$ Values[a]

| | antibody: | | | | | | | | | | |
|---|---|---|---|---|---|---|---|---|---|---|---|
| | Sol-8 | Sol-48 | Sol-54 | Sol-55 | Sol-59 | Sol-67 | Sol-68 | Sol-71 | Sol-91 | Sol-106 | Sol-129 |
| | | | | | | isotype: | | | | | |
| Compd | IgG2a | IgG2a | IgG2a | IgG2a | IgG2a | IgG1 | IgG1 | IgG2a | IgG2a | IgG2a | IgG1 |
| solanidine | 46 ± 6.4 | 18 ± 4.4 | 131 ± 53 | 60 ± 19 | 16 ± 1.7 | 15.6 | 489 ± 73 | 1020 ± 500 | 36 ± 5.7 | 14 ± 2.4 | 2.5 ± 0.35 |
| α-solanine | 253 ± 64 | 436 ± 135 | 215 ± 32 | 118 ± 18 | 35 ± 8 | 27.8 | nc | nc | 104 ± 18 | 49 ± 8 | 2.6 ± 0.25 |
| α-chaconine | 294 ± 34 | 323 ± 125 | 165 ± 58 | 204 ± 19 | 25 ± 2.1 | 20.2 | nc | nc | 82 ± 5.2 | 54 ± 13 | 2.8 ± 0.2 |
| solasonine | nc[b] | nc | nc | nc | nc | nc | nc | nc | nc | nc | 36 ± 3.2 |
| α-tomatine | nc | nc | nc | nc | nc | nc | nc | nc | nc | nc | 5.4 ± 3.5 |
| tomatidine | nc | nc | nc | nc | nc | nc | nc | nc | nc | nc | 10.4 ± 2.0 |
| digitonin | nc | nd[c] | nc | nc | nc | nc | nc | nc | nc | nc | nc |
| cholesterol | nc | nd | nc | nc | nc | nc | nc | nc | nc | nc | nc |
| stigmasterol | nc | nd | nc | nc | nc | nc | nc | nc | nc | nc | nc |
| β-sitosterol | nc | nd | nc | nc | nc | nc | nc | nc | nc | nc | nc |

[a]$IC_{50}$ values in ppb ± one standard deviation.
[b]nc, no competition at 10,000 ppb.
[c]nd, not done.

TABLE 2

Glycoalkaloid Levels (Milligrams per Gram of Fresh Weight) Measured in Potato Samples

| | HPLC | | ELISA (total GA[a]) | |
|---|---|---|---|---|
| sample | α-chaconine | α-solanine | Sol-106 | Sol-129 |
| 1 | tr | 0 | 0.015 | 0.004 |
| 2 | 0.1 | 0.1 | 0.13 | 0.13 |
| 3 | 0.5 | 0.3 | 0.5 | 0.97 |
| 4 | 0.8 | 0.5 | 0.6 | 1.63 |
| 5 | 2.1 | 0.8 | >2.0 | >2.5 |

[a]total glycoalkaloids expressed as glycoalkaloid equivalents, the sum of α-chaconine and α-solanine

TABLE 3

Analysis of α-Tomatine in Freeze-dried Tomatoes (μg/sample)

| SAMPLE | HPLC | ELISA |
|---|---|---|
| Control Red Tomato | 6.0 | 6.7 ± 0.4 |
| Mature Green Control Tomato | 12.2 | 11.5 ± 0.9 |
| Manteca Red Tomato | 1.0 | 1.13 ± 0.09 |
| Manteca Green Tomato | 30.8 | 31.2 ± 3.1 |
| Precipitated Control Red Tomato | 1.9 | 1.5 ± 0.2 |
| Immature Green Tomato | 16.8 | 17.3 ± 1.3 |
| Immature Green Tomato Replicate | 19.2 | 20.4 ± 0.44 |
| Mature Green Tomato | 3.9 | 3.9 ± 0.22 |
| Mature Green Tomato Replicate | 3.8 | 3.7 ± 0.20 |
| Breaker Tomato | 6.1 | 5.9 ± 0.15 |
| Breaker Tomato Replicate | 9.2 | 9.0 ± 0.15 |
| Large Immature Tomato | 40.9 | 40 ± 2.75 |
| Large Immature Tomato Replicate | 38.5 | 37.1 ± 0.96 |
| Tomato Plant Roots | 32.0 | 30.8 ± 1.45 |
| Tomato Plant Roots Replicate | 35.3 | 34.7 ± 0.78 |
| Tomatillos | 0.6 | 0.62 ± 0.01 |
| Tomatillos Replicate | 0.6 | 0.61 ± 0.02 |
| Canned Tomato Sauce | 6.4 | 5.7 ± 0.18 |
| Pickled Tomatoes | 12.1 | 11.4 ± 0.25 |
| Commercial Mature Green Tomatoes | 14.4 | 13.5 ± 0.23 |

We claim:

1. A hybridoma cell line ATCC HB 12201 which produces and secretes monoclonal antibody Sol-129 which selectively binds to the potato glycoalkaloids α-solanine and α-chaconine, the eggplant glycoalkaloid solasonine, and the tomato glycoalkaloid α-tomatine.

2. Monoclonal antibody Sol-129 produced by the hybridoma cell line of claim 1.

3. A method for detecting or quantifying glycoalkaloids of potatoes, tomatoes, eggplants or mixtures thereof in a biological sample comprising:

(a) contacting said sample with monoclonal antibody Sol-129 which is produced by the hybridoma cell line of claim 1, to form a glycoalkaloid/antibody immunocomplex when glycoalkaloids of potatoes, tomatoes, eggplants or mixtures thereof are present, and (b) detecting the presence or amount of said immunocomplex.

4. The method of claim 3 wherein said sample is selected from the group consisting of potatoes, tomatoes, eggplants, cultivars of potatoes, tomatoes or eggplants, foods comprising processed potato, tomato or eggplant products, and animal or human tissues or fluids.

5. The method of claim 3 wherein said contacting step comprises:

(1) providing a solid substrate having one or more of potato glycoalkaloids, tomato glycoalkaloids or eggplant glycoalkaloids bound thereto;

(2) incubating said sample with said solid substrate and said monoclonal antibody; and (3) rinsing said support; and wherein said detecting step comprises:

(4) detecting any monoclonal antibody bound to said support; and (5) determining the presence or amount of potato, tomato, and eggplant glycoalkaloids in said sample.

6. A kit for the detection or quantification of the glycoalkaloids of potatoes, tomatoes, eggplants or mixtures thereof in a biological sample comprising monoclonal antibody Sol-129 which is produced by the hybridoma cell line of claim 1.

* * * * *